US010113961B2

(12) United States Patent
Pavillon et al.

(10) Patent No.: US 10,113,961 B2
(45) Date of Patent: Oct. 30, 2018

(54) APPARATUS AND METHOD FOR QUANTITIVE PHASE TOMOGRAPHY THROUGH LINEAR SCANNING WITH COHERENT AND NON-COHERENT DETECTION

(71) Applicant: ECOLE POLYTECHNIQUE FEDERALE DE LAUSANNE (EPFL), Lausanne (CH)

(72) Inventors: Nicolas Pavillon, Lausanne (CH); Christian Depeursinge, Préverenges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/062,092

(22) Filed: Mar. 5, 2016

(65) Prior Publication Data

US 2017/0023472 A1    Jan. 26, 2017

Related U.S. Application Data

(63) Continuation of application No. 14/235,925, filed as application No. PCT/IB2012/053895 on Jul. 30, 2012.

(30) Foreign Application Priority Data

Jul. 29, 2011 (EP) .................................. 11175966

(51) Int. Cl.
*G01B 9/02* (2006.01)
*G01N 21/45* (2006.01)
(Continued)

(52) U.S. Cl.
CPC ......... *G01N 21/453* (2013.01); *A61B 5/0066* (2013.01); *A61B 5/0073* (2013.01);
(Continued)

(58) Field of Classification Search
CPC ............ G01B 9/02041; G01B 9/02083; G01N 21/45; G01N 21/4795; G03H 1/0443;
(Continued)

(56) References Cited

U.S. PATENT DOCUMENTS

2008/0265130 A1\* 10/2008 Colomb ................... G01J 9/02
250/201.9
2009/0002789 A1\* 1/2009 Lauer ................. G01B 11/2441
359/22

(Continued)

FOREIGN PATENT DOCUMENTS

WO         03/002989 A1     1/2003

OTHER PUBLICATIONS

Gerchberg, R. W. et al. "A Practical Algorithm for the Determination of Phase from Image and Diffraction Plane Pictures". OPTIK, vol. 35, No. 2, 1972, pp. 237-246.\*
(Continued)

*Primary Examiner* — Michael A Lyons
(74) *Attorney, Agent, or Firm* — Nixon & Vanderhye P.C.

(57) ABSTRACT

The disclosed invention describes a new apparatus performing a new data acquisition for quantitative refractive index tomography. It is based on a linear scanning of the specimen, opposed to the classical approaches based on rotations of either the sample or the illumination beam, which are based on the illumination with plane waves, which orientation is successively modified in order to acquire angular information. On the contrary, the inventive apparatus and method rely on a specially shaped illumination, which provides straightforwardly an angular distribution in the illumination (Continued)

of the specimen. The specimen can thus be linearly scanned in the object plane in order to acquire the data set enabling tomographic reconstruction, where the different positions directly possess the information on various angles for the incoming wave vectors.

23 Claims, 12 Drawing Sheets

(51) Int. Cl.
| | |
|---|---|
| A61B 5/00 | (2006.01) |
| G01N 21/47 | (2006.01) |
| G03H 1/08 | (2006.01) |
| G01J 9/00 | (2006.01) |
| G02B 21/00 | (2006.01) |
| G02B 21/02 | (2006.01) |
| G02B 21/08 | (2006.01) |
| G02B 21/36 | (2006.01) |
| G03H 1/00 | (2006.01) |
| G03H 1/04 | (2006.01) |

(52) U.S. Cl.
CPC ..... *G01B 9/02041* (2013.01); *G01B 9/02083* (2013.01); *G01J 9/00* (2013.01); *G01N 21/45* (2013.01); *G01N 21/4795* (2013.01); *G02B 21/0092* (2013.01); *G02B 21/02* (2013.01); *G02B 21/088* (2013.01); *G02B 21/365* (2013.01); *G03H 1/0005* (2013.01); *G03H 1/0443* (2013.01); *G03H 1/0866* (2013.01); *G01N 2021/458* (2013.01); *G01N 2201/12* (2013.01); *G03H 2001/005* (2013.01); *G03H 2001/0456* (2013.01)

(58) Field of Classification Search
CPC .......... G03H 1/0866; G03H 2001/005; G03H 2001/0456; A61B 5/0066; A61B 5/0073
See application file for complete search history.

(56) References Cited

U.S. PATENT DOCUMENTS

| | | | | |
|---|---|---|---|---|
| 2009/0125242 A1* | 5/2009 | Choi | ..................... | G01N 21/45 702/19 |
| 2012/0069345 A1* | 3/2012 | Shaffer | ................ | G01B 11/002 356/457 |
| 2013/0057869 A1* | 3/2013 | Cotte | .................. | G02B 21/365 356/457 |

OTHER PUBLICATIONS

Teague, Michael Reed. "Image formation in terms of the transport equation". J. Opt. Soc. Am. A, vol. 2, No. 11, Nov. 1985, pp. 2019-2026.*
Charrière, Florian et al. "Cell refractive index tomography by digital holographic microscopy". Optics Letters, vol. 31, No. 2, Jan. 15, 2006, pp. 178-180.*
Bon, Pierre, et al., "Quadriwave lateral shearing interferometry for quantitative phase microscopy of living cells," Optics Express, Jul. 20, 2009, vol. 17, No. 15, pp. 13080-13094.
Born M. et al.' Principles of Optics, 7th Edition, 1999, Chapter XIII "Scattering from inhomogeneous media," pp. 694-733.
Charrière, Florian, et al., "Living specimen tomography by digital holographic microscopy: morphometry of testate amoeba," Optics Express, Aug. 7, 2006, vol. 14, No. 16, pp. 7005-7013.
Choi, Wonshik, et al., "Tomographic phase microscopy," Nature Methods, Sep. 2007, vol. 4, No. 9, pp. 717-719.
Dändliker, R., et al., "Reconstruction of the Three-Dimensional Refractive Index from Scattered Waves," Optics Communications, Feb. 1970, vol. 1, No. 7, pp. 323-328.
Devaney, A. J., "A Filtered Backpropagation Algorithm for Diffraction Tomography," Ultrasonic Imaging, 1982, vol. 4, pp. 336-350.
Fienup, J. R., "Phase retrieval algorithms: a comparison," Applied Optics, Aug. 1, 1982, vol. 21, No. 15, pp. 2758-2769.
Indebetouw, Guy, et al., "Space-time digital holography: A three-dimensional microscopic imaging scheme with an arbitrary degree of spatial coherence," Applied Physics Letters, Oct. 4, 1999, vol. 75, No. 14, pp. 2017-2019.
Kak, Avinash C., et al., "Principles of Computerized Tomographic Imaging," Society for Industrial and Applied Mathematics, 2001, 12 pages.
Kou, Shan Shan, et al., "Image formation in holographic tomography," Optics Letters, Oct. 15, 2008, vol. 33, No. 20, pp. 2362-2364.
Simon, Bertrand, et al., "Holographic microscopy and diffractive microtomography of transparent samples," Meas. Sci. Tech, 2008, vol. 19, 13 pages.
Sung, Yongjin, et al., "Optical diffraction tomography for high resolution live cell imaging," Opt Express, Jan. 5, 2009, vol. 17, No. 1, 15 pages.
Vertu, Stanislas, et al., "Diffraction microtomography with sample rotation: influence of a missing apple core in the recorded frequency space," Cent. Eur. J. Phys., 2009, vol. 7, 7 pages.
Wolf, Emil, "Three-Dimensional Structure Determination of Semi-Transparent Objects from Holographic Data," Optics Communications, Sep./Oct. 1969, vol. 1, No. 4, pp. 153-156.
Yang, Guo-zhen, et al., "Gerchberg-Saxton and Yang-Gu algorithms for phase retrieval in a nonunitary transform system: a comparison," Applied Optics, Jan. 10, 1994, vol. 33, No. 2, pp. 209-218.

* cited by examiner

BACKGROUND ART

APPARATUS AND METHOD FOR QUANTITIVE PHASE TOMOGRAPHY THROUGH LINEAR SCANNING WITH COHERENT AND NON-COHERENT DETECTION

This application is a continuation of U.S. patent application Ser. No. 14/235,925, filed 29 Jan. 2014, which is the U.S. national phase of International Application No. PCT/IB2012/053895, filed 30 Jul. 2012, which designated the U.S. and claims priority to European Application No. 11175966.8 filed 29 Jul. 2011, the entire contents of each of which are hereby incorporated by reference.

FIELD OF THE INVENTION

The disclosed invention relates to an apparatus and a method that perform a data acquisition for quantitative refractive index tomography.

BACKGROUND OF THE INVENTION

The manner in which the inventive apparatus or method proceeds is based on a linear scanning of the specimen, as opposed to known classical approaches which are based on rotations of either the sample or the illumination beam, which are based on the illumination with plane waves, which orientation is successively modified in order to acquire angular information. On the contrary, the inventive apparatus or method relies on a specially shaped illumination, which provides straightforwardly an angular distribution in the illumination of the specimen. The specimen can thus be linearly scanned in the object plane in order to acquire the data set enabling tomographic reconstruction, where the different positions directly possess the information on various angles for the incoming wave vectors. As the standard methods for tomographic reconstruction are typically assuming a plane illumination, the proposed approach requires a dedicated reconstruction method, which takes into account the wave profile employed for illumination, either by pre-processing the measured information to enable its use through standard methods, or by employing specific methods directly considering the particular engineered illumination employed. As for standard methods, the proposed approach based on a specially engineered illumination called structured wavefront and linear scanning can be employed through a so-called projection formalism, in which a real measurement of either the amplitude or the phase of the wave having interacted with the specimen can provide the three-dimensional distribution of respectively the absorption or the refractive index of the specimen. It is also possible to employ more general formalisms considering the diffraction theory, in which case a measurement of the full information of the wave (amplitude and phase) is required for tomographic reconstruction of the three-dimensional dielectric information of the specimen.

The theoretical foundations for tomography based on coherent imaging were proposed at the end of the sixties by Wolf and then Dändliker et al. (Wolf, 1969; Dändliker and Weiss, 1970). These seminal publications stated the relations between multiple frames acquired in various conditions—such as different illumination angles or different monochromatic wavelengths—and the information they provide on the three-dimensional volume, based on a diffraction formalism. In order to enable an analytical representation of the problem, one has usually to resort to an approximation of diffraction at first order, chosen either as the Born or as the Rytov approximations, as described for example in Born and Wolf, 1999.

The problem of resolving the integrated information along the optical axis in microscopy has been addressed in many various ways in the last decades, through typically different implementations enabling sectioning along the optical axis. One of the most widely known methods enabling sectioning is confocal microscopy, where the out-of-focus information is discarded before acquisition. While this type of methods enable 3D imaging in microscopy, they rely on principles of optical sectioning, which are not directly related to the approach of the proposed method. The sectioning typically requires the detection of a small 3D volume coupled with scanning procedures to recover the 3D information. Another widely known approach is the optical coherence tomography (OCT). As its name indicates, it is based on the exploitation of coherence properties of the light source with an interferometric detection scheme. OCT methods are based typically on reflection measurements, and rely on the spectral bandwidth of coherent light to generate an optical sectioning effect.

On the contrary of these known three-dimensional imaging methods, which are based on a sectioning property at detection, the proposed approach relies on the full-field detection of wave fields scattered by the specimen illuminated at various angles, which can be combined at post-processing stage in order to synthetically reconstruct the three-dimensional information. In this context, the first reconstruction methods proposed for practical applications were based on computer tomography (CT)—commonly called straight ray tomography—thus neglecting diffraction (Kak and Slaney, 1987). The use of this type of algorithm was justified by their extensive use for CT applications. Similar methods taking into account light diffraction were also proposed (Devaney, 1982).

In the context of microscopy, two main approaches were explored for acquisition of data based on angular scanning, consisting either in rotating the object, or to scan the beam around the object. These two methods were explored in various studies (Noda et al., 1992; Lauer, 1998; Lauer, 1999), and lead to different reconstruction resolutions. The two methods however rely always on the fundamental approach proposed in the sixties, and thus always require planar waves for illumination. Recently, various applications could be demonstrated with these methods, leading to high resolution with both the object rotation (Charrière et al., OL, 2006; Charrière et al., OX, 2006) and with the beam scanning (Choi, 2007; Debailleul, 2008; Sung, 2009).

SUMMARY OF THE INVENTION

The present invention provides an apparatus and a method as described in the appended independent and dependent claims.

The disclosed invention describes a new apparatus performing a new data acquisition for quantitative refractive index tomography. It is based on a linear scanning of the specimen, as opposed to the classical approaches based on rotations of either the sample or the illumination beam, which are based on the illumination with plane waves, the orientation of which is successively modified in order to acquire angular information. On the contrary, the proposed apparatus relies on a specially shaped illumination, which provides straightforwardly an angular distribution in the illumination of the specimen. The specimen can thus be linearly scanned in the object plane in order to acquire the data set enabling tomographic reconstruction, where the different positions directly possess the information on waves scattered at various angles of the incoming wave vectors. As the standard methods for tomographic reconstruction are typically assuming a plane illumination, the proposed approach requires a dedicated reconstruction method, which takes into account the wave profile employed for illumination, either by pre-processing the measured information to enable its use through standard methods, or by employing specific methods directly considering the particular structured illumination employed. As for standard methods, the proposed approach based on structured illumination and linear scanning can be employed through a so-called projection formalism, in which a real measurement of either the amplitude or the phase of the wave having interacted with the specimen can provide the three-dimensional distribution of respectively the absorption or the refractive index of the specimen. It is also possible to employ more general formalisms considering the diffraction theory, in which case a measurement of the full information of the wave (amplitude and phase) is required for tomographic reconstruction of the three-dimensional dielectric information of the specimen.

BRIEF DESCRIPTION OF THE DRAWINGS

FIG. 1 (a) illustrate the measurement of the transmitted light beam, whereas FIG. 1.(c) illustrates the measurement of both reflected and transmitted beams simultaneously by the recourse to two identical high NA MO's.

DETAILED DESCRIPTION OF THE INVENTION

A more detailed description of the figures will now be given and followed by a description of example embodiments of the invention.

Figure 1A:
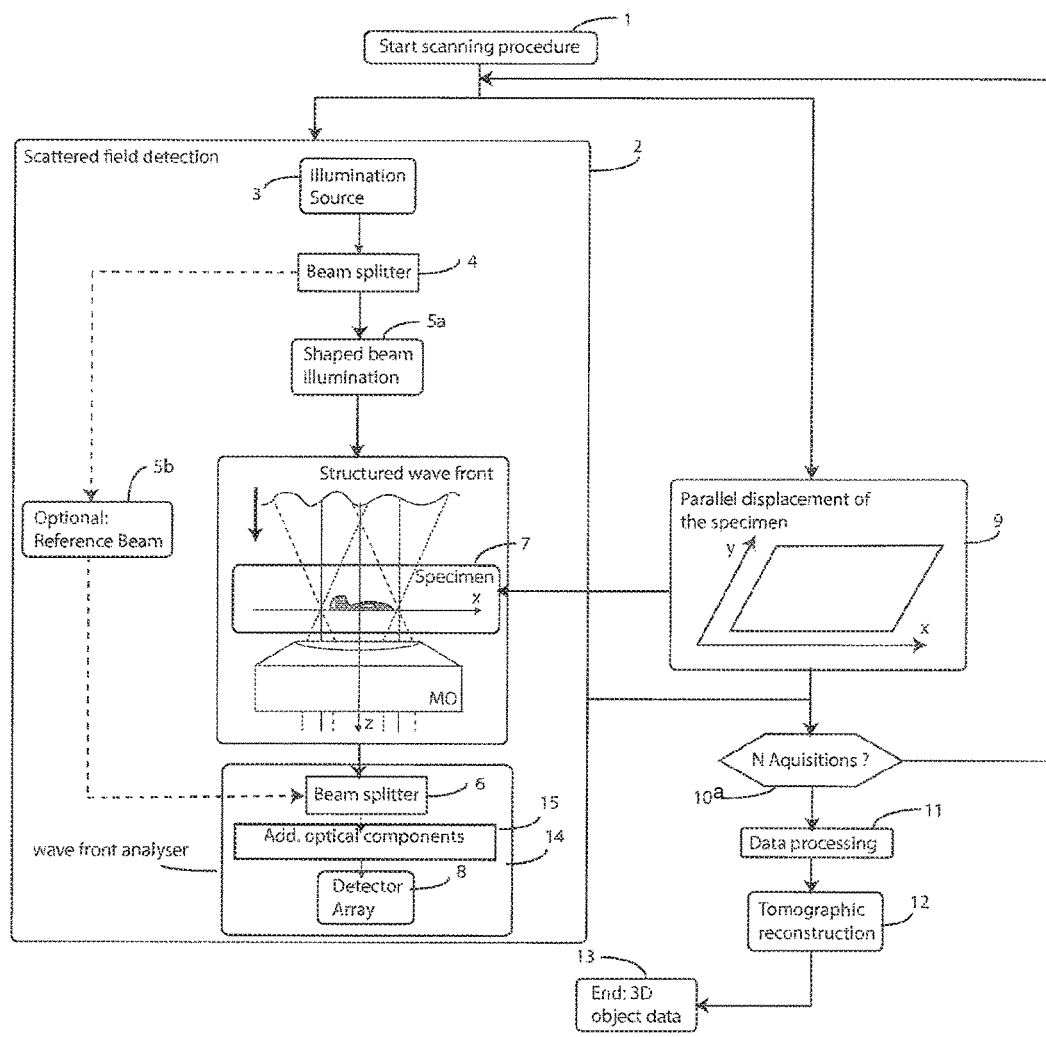
FIG. 1 gives a broad outline of the process disclosed in the present invention, according to an example embodiment.
FIG. 1(b) illustrates the measurement of the reflected light beam.
Figure 1B:
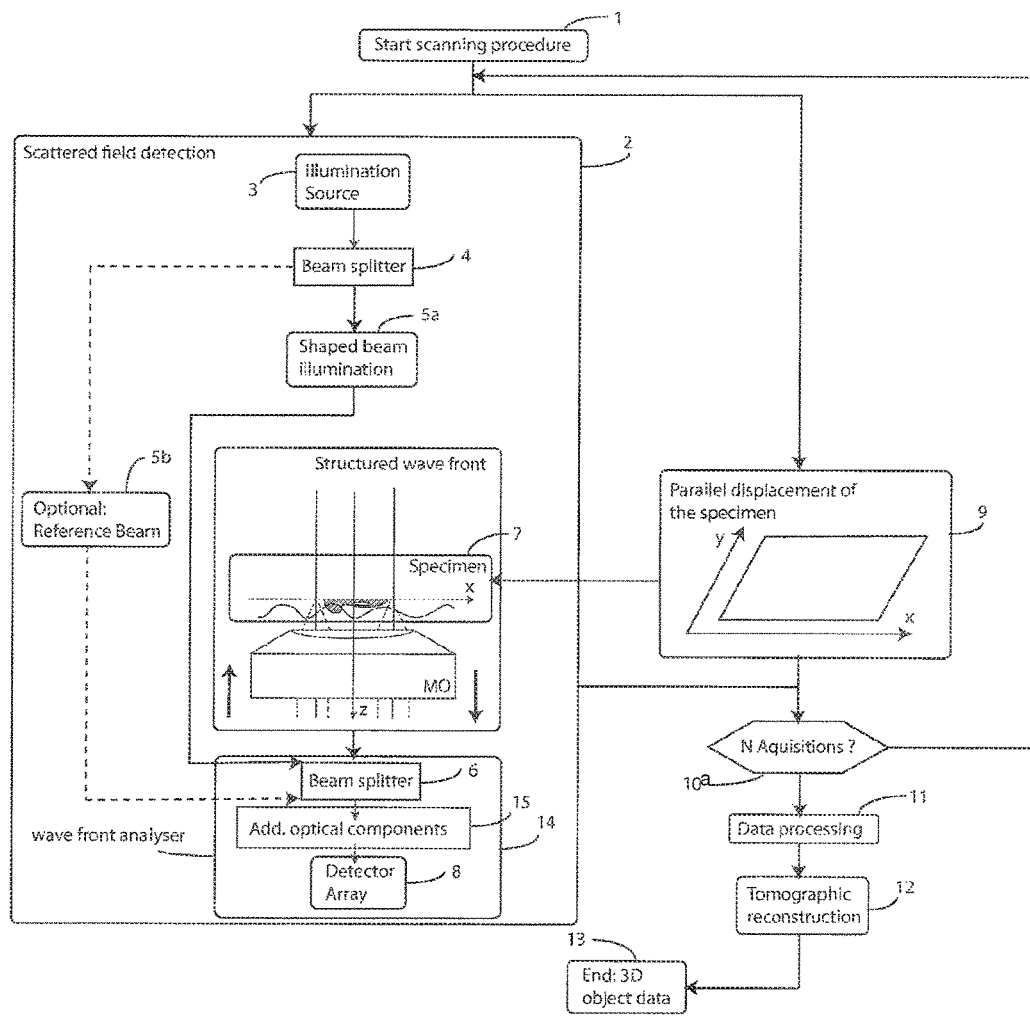

FIG. 1 gives a broad outline of the process disclosed in the present invention: starting a scan procedure at box 1 starts an acquisition of a data array permitting the reconstruction of the field scattered by the specimen, as shown in box 2. After a first acquisition, the specimen is slid in parallel along a predefined direction by actuating a X-Y translation stage as represented in box 9. The loop 2-9 is then iterated till the number of acquired data arrays reaches a predefined number N as shown in box 10a. Then, the stack of N data arrays is processed in box 11 in a hereby disclosed manner so that a full 3D image of the specimen is obtained in box 12, which marks the end of the process at box 13. Box 2 discloses in more details the method and apparatus of the present invention: an Illumination source 3 delivers an optical beam which is shaped in box 5a by an appropriate optical component and the wavefront of which is structured in a particular manner before illuminating the specimen at box 7. In a preferred embodiment, a strongly convergent beam is used as structured wavefront to illuminate the specimen. The scattered light is then collected by a Microscope Objective (MO) and transmitted to, in the most general case, a so-called wave front analyser (box 14), which can serve to measure the complex wavefield of the scattered light. The wavefront analyser is in general composed of a structured optical element: in a Hartmann-shack analyser, it is an array of microlenses, in a more sophisticated analyser (quadriwave lateral shearing interferometer), a bidimensional grating can be used or more generally Damman gratings. Face masks in the pupil plane of the MO can also be used: spiral phase in particular, providing thereby a phase gradient which can permit the phase restoration by integration. Common path interferometers can be used also to analyse the wave front: filtered beam used as reference wave (Indebetouw, A P L, 1999) diffraction microscopy (Popescu, O L, 2006) and SLIM (Wang, O X, 2011) have been proposed and can be use as wave front analyser in the proposed invention. It must be pointed out that Hartmann Shack analysers are performing with multicolour wave fronts and actually do not require coherent waves to characterise the wave fronts. Further so-called "incoherent" wave front analysers have been developed to characterise incoherent or partially coherent waves. TIE (transport of intensity equation) allow the determination of the propagating wave field direction at each point of the wave front and phase can be computed for a monochromatic wave.

In a preferred embodiment, an holographic approach (DHM based) has been selected to establish the feasibility of the invention: in this case, an optional reference beam 5b can be derived from the illumination source of box 3 by a beam splitter in box 4 and recombined with the beam scattered by the specimen by another optional beam splitter at box 6, permitting thereby the coherent detection of the scattered beam and the reconstruction of the wavefront in amplitude and phase.

Finally, a detector array in box 8, in general an electronic camera, provides the untreated signal, before being acquired by a computer (not shown in FIG. 1).

Three variants of the inventions can be implemented:

FIG. 1 (a) illustrates the case of a transmitted structured beam: the instrument performs well for transparent or semi-transparent specimens.

FIG. 1 (b) illustrates the case of a reflected structured beam: the instrument performs well for non-transparent or semi-transparent specimens backscattering light. In this case, the MO used as the condenser shaping the structured light is also used as the collecting MO. A beam splitter can be used to inject the illuminating beam in the MO. The uss of a polarising beam splitter can help in the elimination of the parasitic light backscattered in the MO itself.

Figure 1C:
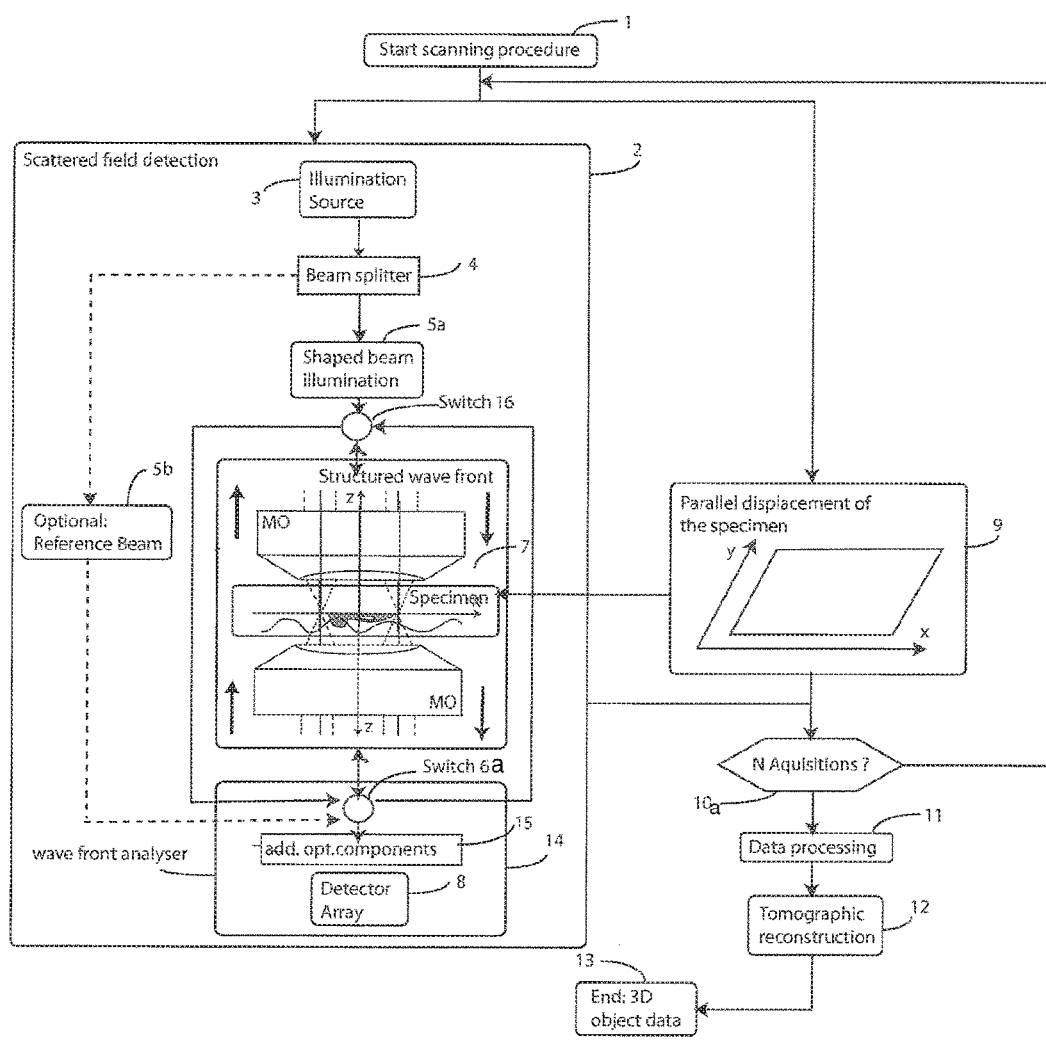

It must be emphasized that a combination of the arrangement of FIG. 1 (a) and FIG. 1 (b) can be combined (see FIG. 1(c) in order to provide data on the Ewald sphere on both cups corresponding to forward and backward scattered light in the Fourier space. Two possibly identical high NA MO are used in a piggy back configuration (sometimes call 4π). Two wave front analysers, including the camera should be added symmetrically at the output pupil of each MO. Two switches 6a and 16 can optionally help to reverse the converging illumination beam direction. This last configuration could provide a device to provide full. 4π capabilities in diffraction tomography.

Figure 2:
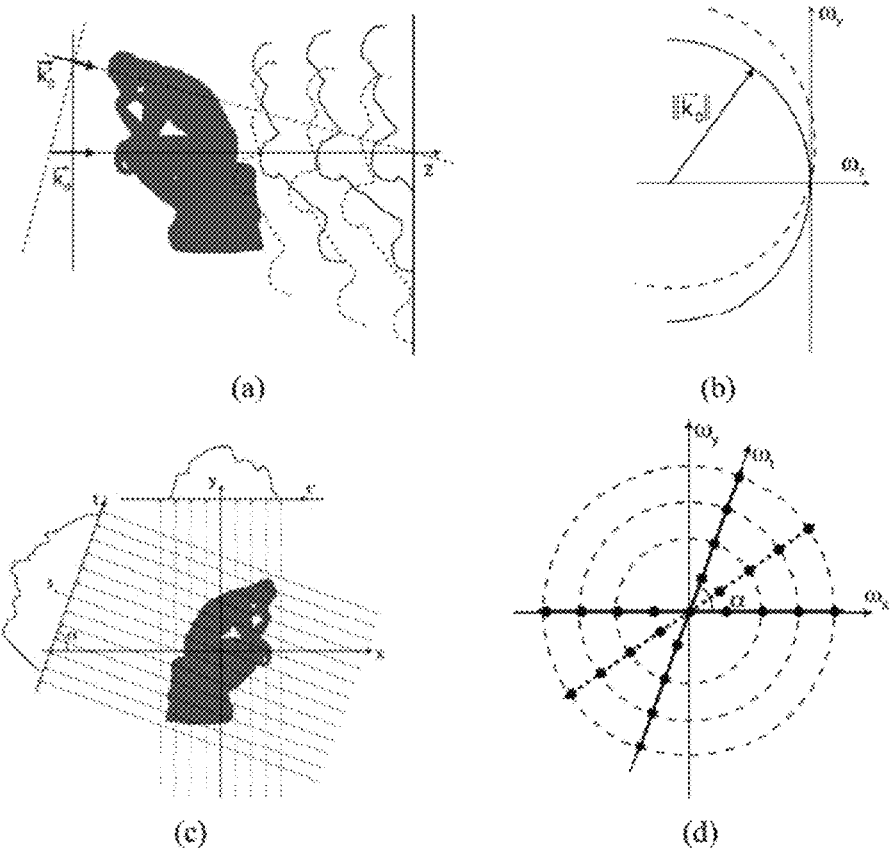
FIG. 2 represents the fundamental measurement scheme of classical quantitative refractive index tomography, shown here in the 2D case for the sake of simplicity.

FIG. 2 represents the fundamental measurement scheme of classical quantitative refractive index tomography, shown here in the 2 Dimensional (2D) case for the sake of simplicity:
(a) illumination at various angles of plane waves with measurement of the scattered field;
(b) corresponding spatial frequencies for an angular view, situated on half a circle when considering first-order diffraction;
(c) graphical representation of the illumination with various angles when considering projections
(d) corresponding in the spectral domain to lines when neglecting diffraction.

Figure 3:
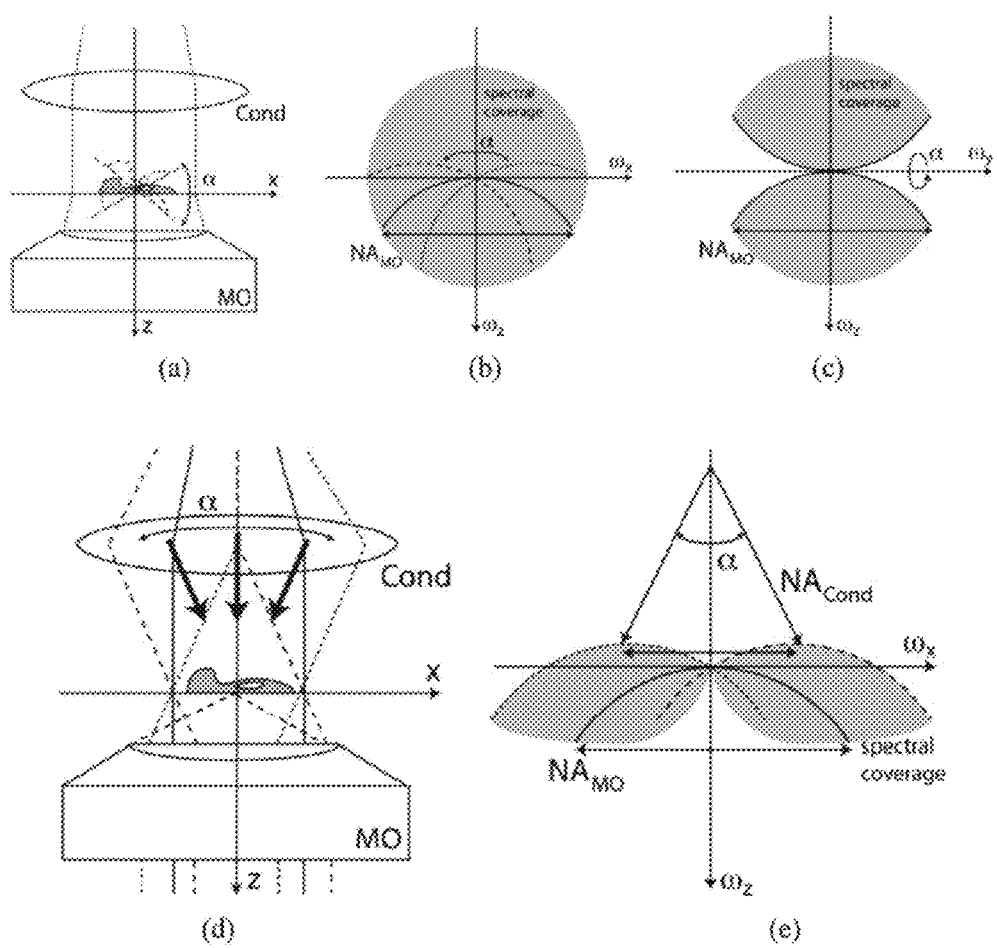
FIG. 3 represents a tomographic acquisition through classical plane wave excitation.

FIG. 3 represents a tomographic acquisition through classical plane wave excitation:
(a) object rotation method, with (b-c) the corresponding frequency space filling shown by 2D projections perpendicular to
(b) the axis $\omega_y$ and
(c) the axis $\omega_x$;
(d) beam scanning method, with
(e) the corresponding frequency space filling shown in 2D projection, where the coherent transfer function is cylindrically symmetric around.

Figure 4:
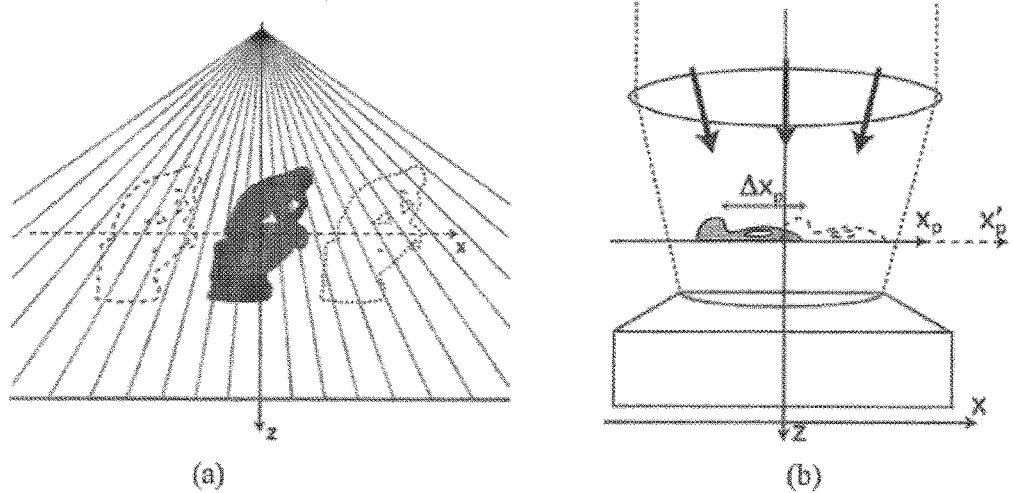
FIG. 4 represents (a) a tomographic acquisition under the proposed method, and (b) a typical conceptual implementation for microscopy.

FIG. 4 represents
(a) a tomographic acquisition under the proposed method, where the object is scanned within an angular distribution of propagation vectors, shown here for the case of a point-source;
(b) typical example and schematic implementation for microscopy, where a spherical wave is employed as an angular distribution by using a convergent beam emitted by a lens.

Figure 5:
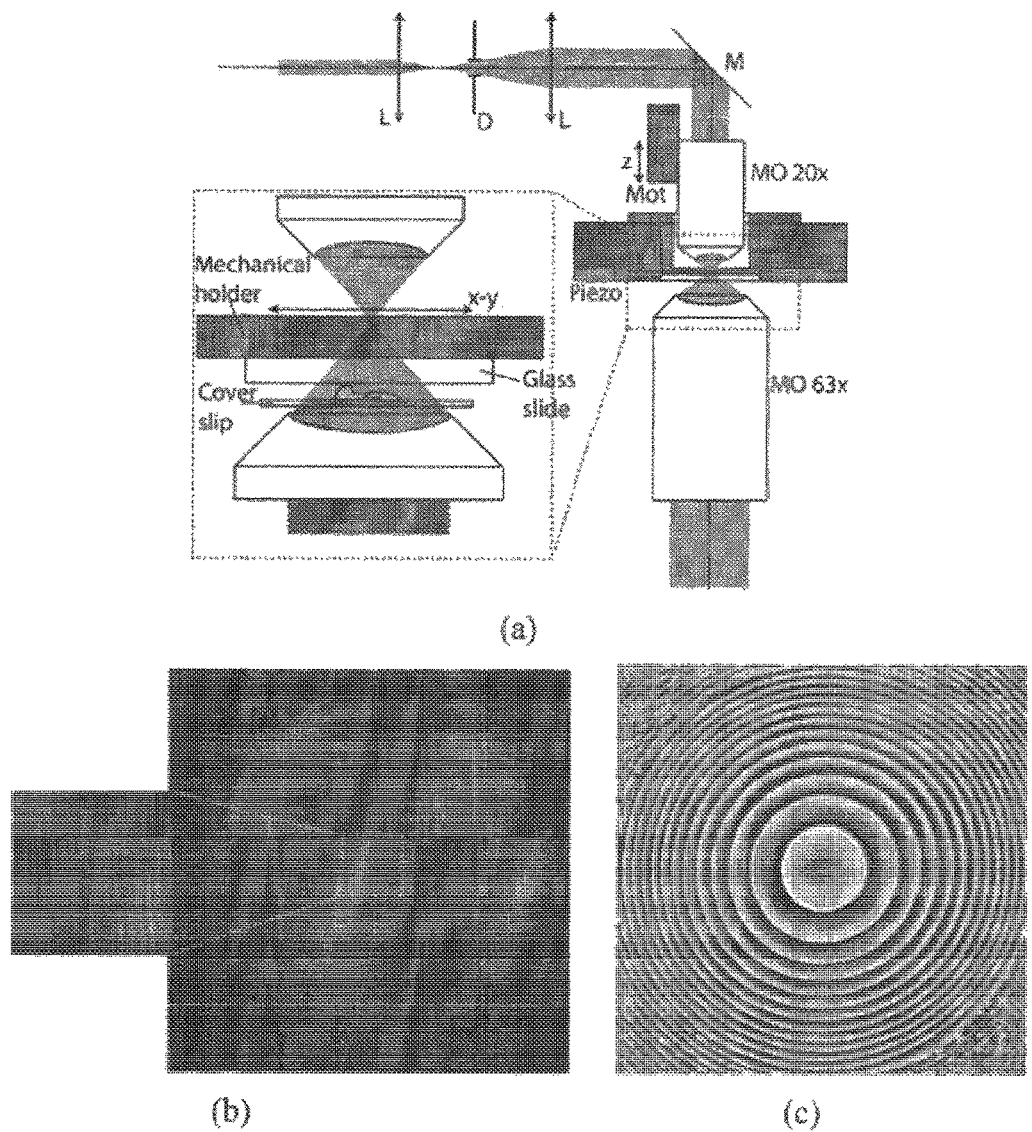
FIG. 5 is (a) typical example of implementation for linear scanning tomography, (b) a typical raw measurement obtained with the configuration presented in (a), and (c) a reconstructed phase profile reconstructed from the data in (b)

FIG. 5 shows
(a) a typical example of implementation for linear scanning tomography, where the angular distribution of the illuminating beam is generated with large angles by a microscope objective as condenser, with the object scanned with a piezo-electric. D: Diaphragm, L: Lens, M: Mirror, Mot: Linear Motor, Piezo: 3D closed-loop piezo-electric stage. Either mechanical (motor) or piezo-actuators can be used alone or together.
(b) typical raw measurement obtained with the configuration presented in (a); and
(c) reconstructed phase profile reconstructed from the data in (b), where one can identify observe the angular distribution in the phase profile.

Figure 6:
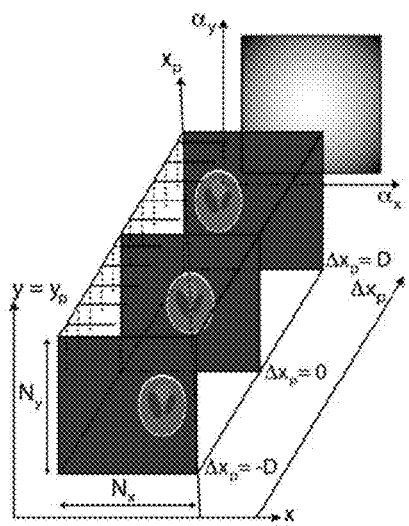
FIG. 6 shows (a) a typical data stack acquired through linear scanning of the object, (b-c) an example of data treatment for tomographic reconstruction.
Figure 6:
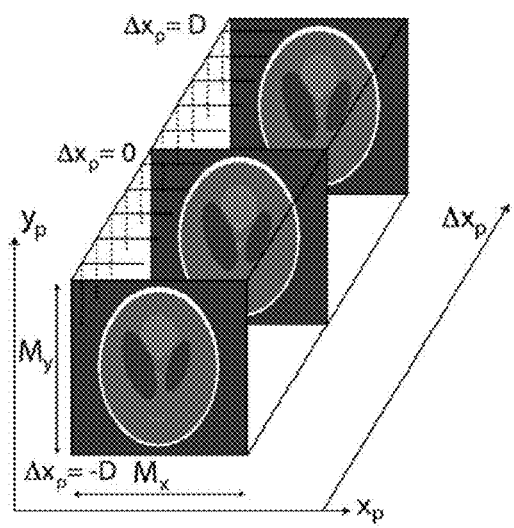
Figure 6:
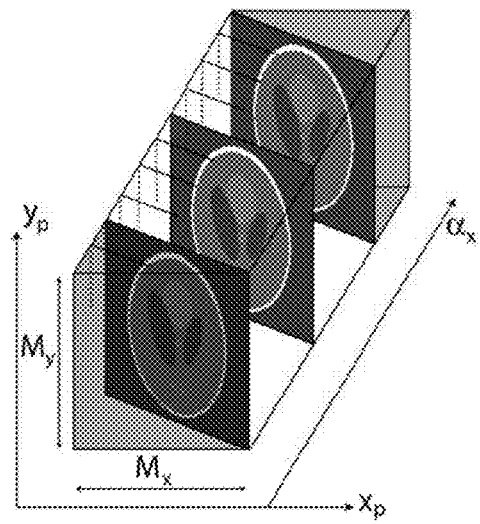

FIG. 6 shows
(a) a typical data stack acquired through linear scanning of the object, where each part of the object is illuminated with another angle for each scanning position.
(b-c) Example of data treatment for tomographic reconstruction, where the data set results from:

(b) first translating the image to obtain an object in a fixed position, and
(c) then rearrange the data to synthetically obtain a constant angular view at each frame.

Figure 7:
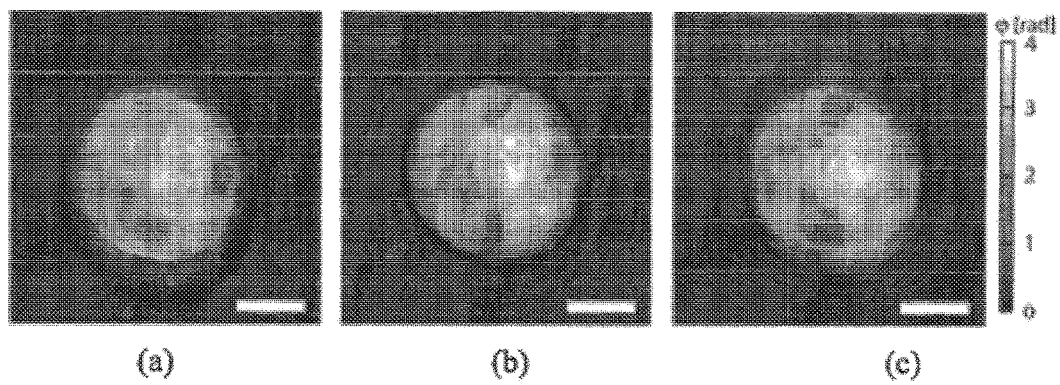
FIG. 7 shows examples of images reconstructed after scanning.

FIG. 7 contains composed examples of images reconstructed after scanning, where the proposed data arrangement provides a synthetic constant angular excitation for each frame:
(a) −15 degree;
(b) −0.3 degree; and
(c) 14.4 degree.

The presented sample is a pollen grain, immersed in glycerol. Scale bars are 5 μm, and the image scale is in radians.

Figure 8:
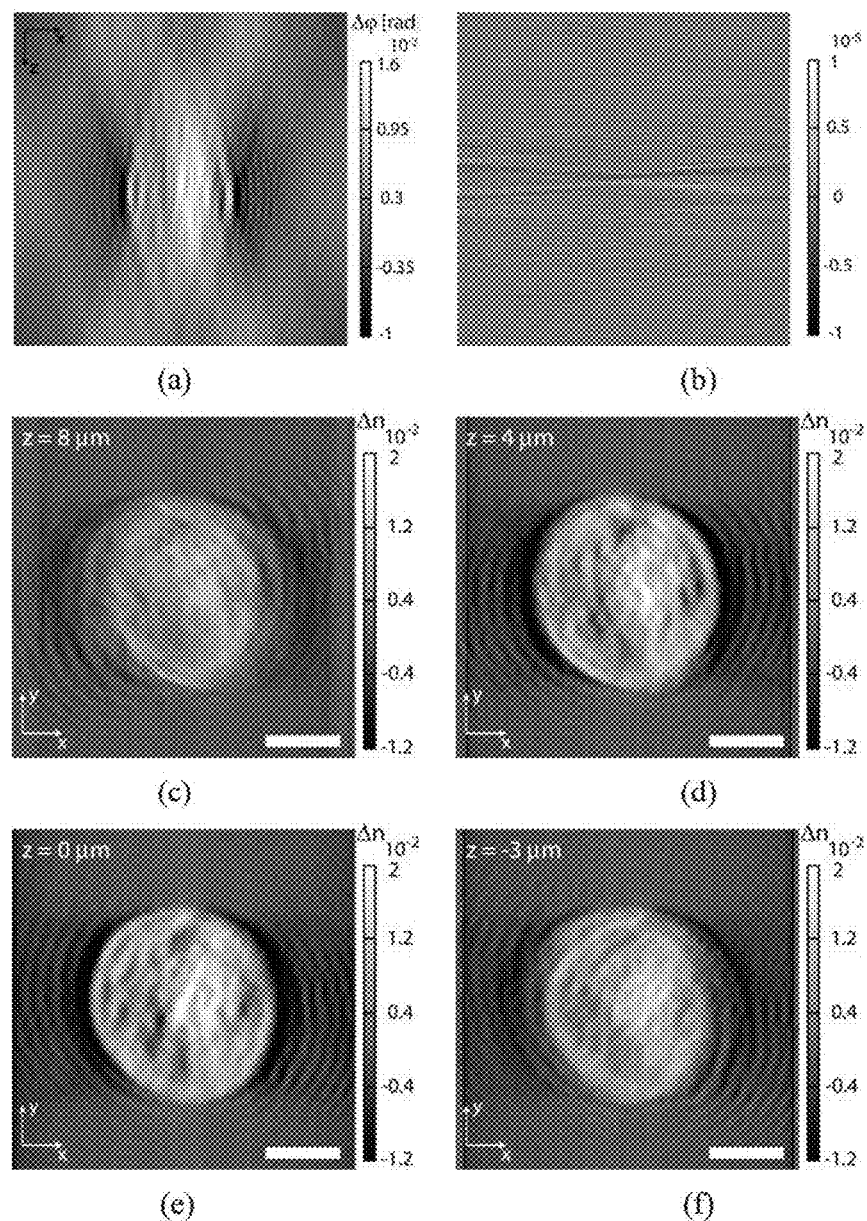
FIG. 8 is an example of tomographic reconstruction from the whole data set of FIG. 7.

FIG. 8 shows an example of tomographic reconstruction from the whole data set of FIG. 7. (a-b) x-z section at the centre of the pollen grain after tomographic inversion with
(a) the real part of the Fourier inversion, shown in radians per voxel, and
(b) the imaginary part of the inversion being nearly negligible.
(c-e) x-y sections of the pollen grain at
(c) z=8 μm;
(d) z=4 μm;
(e) z=0 μm; and
(f) z=−3 μm.

The scales are given in relative refractive index in regards to the immersion medium (glycerol, n=1.473), and scale bars are 5 μm.

Figure 9:
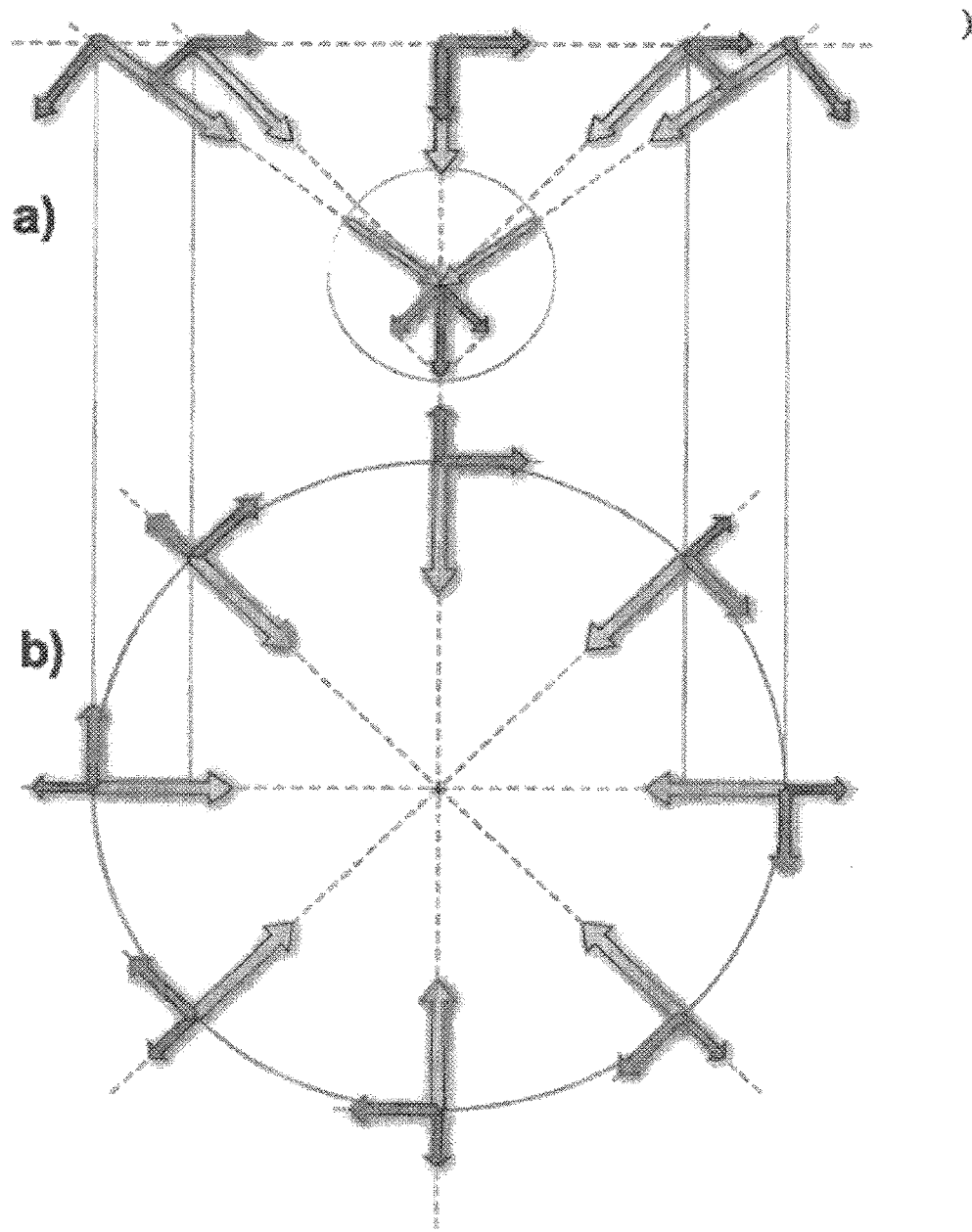
FIG. 9 illustrates the distribution of the electric and magnetic fields in a radially polarised illuminating field.

FIG. 9 illustrates the distribution of the electric field in a radially polarised illuminating field:
a) describes the projection on a plane parallel to the optical axis;
b) features the projection on a plane normal to the optical axis. The distribution of the wavevector (light grey arrow), and associated electric field (radially oriented) and magnetic fields (azimuthally oriented) is shown on the figure.

Figure 10:
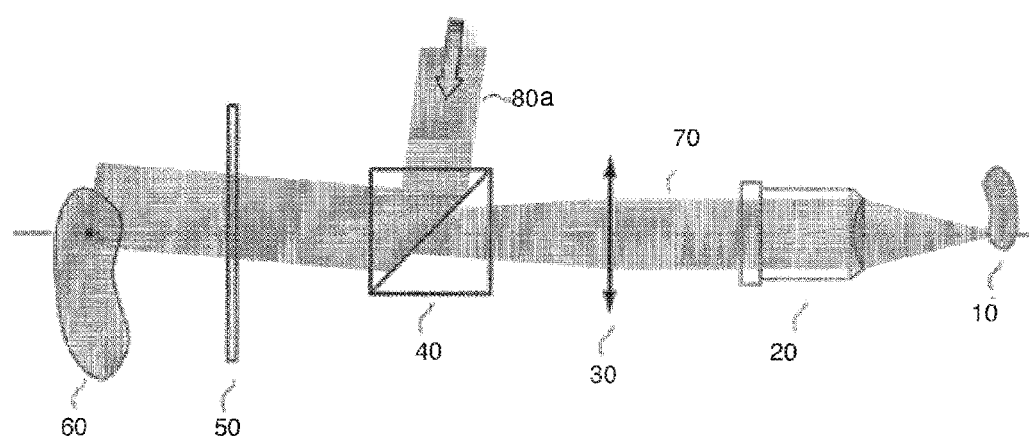
FIG. 10 shows the optical setup to analyse the polarisation components of the diffracted field according to a preferred embodiment.

FIG. 10 shows the optical setup to analyse the polarisation components of the diffracted field: 10 scattering specimen, 20 Microscope objective MO, 30 tube lens, 40 beamsplitter cube, 50 detector array, 60 image of the specimen (beyond, in front of, or in the detector array plane), 70 object beam, 80a reference beam with controlled linear polarisation state.

Figure 11:
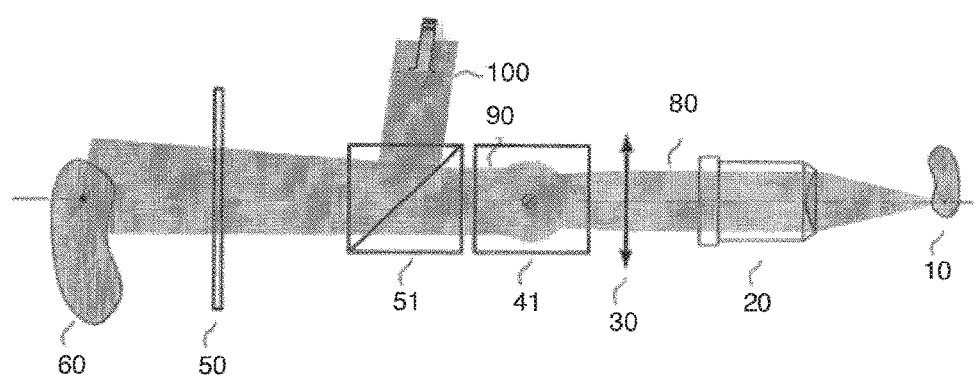
FIG. 11 shows the optical setup to analyse simultaneously the orthogonal polarisation components of the diffracted field according to a further preferred embodiment.
Figure 11:
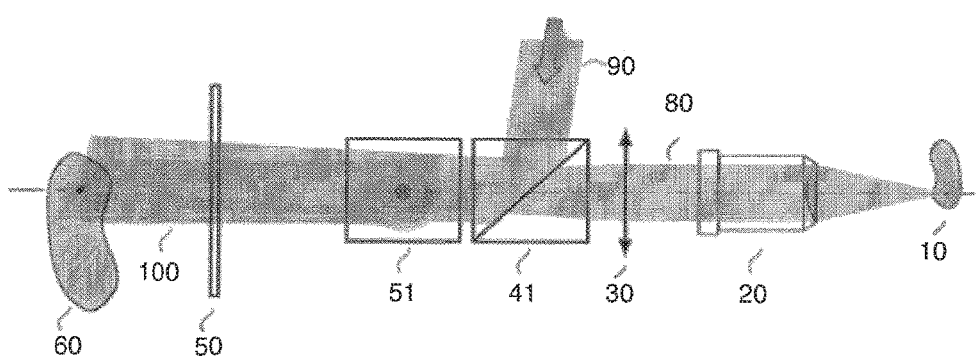

FIG. 11 shows the optical setup to analyse simultaneously the orthogonal polarisation components of the diffracted field:
a) first side projection;
b) orthogonal side projection of the same setup.

For a) and b) the illustrated elements are the following:

| Reference Number | Referenced Element |
| --- | --- |
| 10 | Scattering specimen |
| 20 | Microscope objective MO |
| 30 | Tube lens |
| 41 and 51 | Orthogonally oriented beamsplitter cubes |
| 50 | Detector array |
| 60 | Image of the specimen (beyond, in front of, or in the detector array plane) |
| 80 | Object beam |
| 90 | First reference beam (off-axis) |
| 100 | Second reference beam (off-axis, with approximately the same angle) |

The interference pattern (hologram) is taken in one acquisition and decompose easily in two orthogonal domains in the Fourier space by Fourier analysis.

The first and second reference beams are represented as collimated parallel beams, but may also be convergent spherical beams to match the convergent object beam.

Tomography Principle

The usual approach in tomography consists in taking a plurality of projected images in a plurality of directions. These images are reconstructed from holograms and they are processed digitally in order to extract the tomographic image. Conventionally, the tomographic approach therefore consists in varying the angle of the illumination waves (variable k-vector direction) and to collect the scattered light with a Microscope Objective (MO) having a Numerical Aperture (NA) as large as possible in order to collect high orders of the light scattered by the specimen. Another approach is to rotate the specimen and to collect the scattered light in the high NA microscope objective. In order to avoid these complex manipulations and associated complex optical and mechanical setups, an alternative solution is disclosed in the description of the invention. The main goal of the invention is to replace rotations of either the Illuminating beam or the specimen by a simple linear displacement of the specimen in a specially engineered illuminating beam with a structured wavefront.

The disclosed invention thus describes a new apparatus and a new data acquisition and processing method for quantitative refractive index tomography. It is based on a linear scanning of the specimen, opposed to the classical approaches based on rotations of either the sample or the illumination beam. The pluri-angle illuminations required for tomographic reconstruction are obtained by the recourse to a specially engineered illumination beam with structured wavefront, which can be opposed to the standard plane wave illumination employed in standard approaches. This structured wavefront illumination beam thus provides a continuous distribution of illumination wavevectors inside the field of view, within which the specimen can be simply displaced by linear translation stages. This linear specimen displacement allows retrieving indirectly the pluri-angle views for tomographic reconstruction.

Scattered Beam Acquisition: State of the Art

The standard acquisition consists in acquiring several images at different angles of Incidence, as shown schematically in FIG. 2(a, c). The illumination consists in a plane wave propagating through the specimen, with the scattered wave measured in the far-field on an infinite plane. The measurement process is then repeated for different directions of the propagating vector, in order to retrieve various angular views of the specimen. The main interest of this method lies in the fact that the measurement is made partially or fully for coherent fields, so that the relation between the scattered field and the complex RI (Refractive Index) distribution of the specimen is linear. In the case the complex wave field is measured, the Fourier transform of the measured signal corresponds to the coherent transfer function (CTF) of the field, which can be coherently added with different CTFs, as shown in FIG. 2(b, d), where the addition of different angular distributions generates a distribution of spatial frequencies also in the direction of the optical axis, thus synthetically providing an optical sectioning effect.

While the acquisition principle is similar in both cases, mainly two models are considered to represent the interaction of light with the measured specimen, being either described by the Fourier diffraction theorem (FDT), which takes into account the diffraction of the wave field through the specimen, or by the Fourier slice theorem (FST), which neglects diffraction and considers projections of the field. In both cases, these fundamental theorems relate the spatial frequencies of the measurements taken in the far field and the 3D spectrum of the specimen, as described below. Depending on the type of model used for reconstruction, the spatial frequencies are typically distributed on a line (cf. FIG. 2(d)), corresponding to the case for which diffraction is neglected, or on a cap of circle (cf. FIG. 2(b)), when diffraction at first order is taken into account. The 2D representation in FIG. 2 can be straightforwardly generalised for 3 dimensions (3D).

While being similar in the concept of representation, these two models imply a rather different policy in the acquisition of the information. In the case of the FST, which considers projections, the information retrieved from the wave field can be real-defined, so that the information about the phase shifts induced by the specimen are sufficient for reconstruction. On the other hand, the FDT considers the wave field, implying that a measurement of the full complex wave front in both amplitude and phase is required for reconstruction.

Data Acquisition Strategies: State of the Art

Various scanning implementation can be employed in order to acquire the different angular views required to fill the 3D spatial frequency space in the context of microscopy, and can mainly be divided in two scanning procedures. The two methods however are based on common principles, consisting in illuminating the specimen with plane waves having different directions of propagation vectors.

The first method is based on rotating the object or identically rotating the illumination source around the object, as typically performed in CT scanners. This configuration is shown schematically in FIG. 3(a), with its corresponding spatial frequency filling presented in FIG. 3(b-c), for a rotation along the y axis, and under the FDT formalism. This scanning scheme is characterised by a rather isotropic synthesised 3D CTF thanks to the possibility of rotating the object along the whole $2\pi$ angular range, with typically a missing cone along the direction of rotation, which was coined as a "missing apple core" (Vertu et al., 2009) in literature, as shown in FIG. 3(d). Although the retrieved spatial frequencies are well distributed within the 3D frequency space, this approach suffers from different technical issues. As stated before, the rotation of the object is rather difficult to accomplish precisely, so that the mechanical imprecision during scanning yields a degraded reconstruction. Furthermore, the requirements in space are rather high, so that this approach can only be performed with long working distance MO, thus implying low NA and consequently lower resolution.

On the other hand, the second common scanning strategy consists in scanning the beam through optical means. This is typically performed by scanning the back focal plane of a lens, as depicted in FIG. 3(d). In this fashion, the accessible angular views are limited by the NA of the condenser lens, thus yielding a less efficient filling of the frequency space. Furthermore, this scanning scheme implies that the detection optics, classically taken as a microscope objective, is static while the excitation beam is changing. This implies that the CTF is not rotated, so that the frequencies of each angular view are shifted, as shown in FIG. 3(e), leading to a 3D synthesised CTF in the shape of a "peanut", as denoted in the literature (Kou, 2008). Although being less efficient in the recovery of spatial frequencies in an isotropic way, the beam scanning approach generally leads to better results than object rotation in terms of resolution, due to its better stability during scanning thanks to a static object.

Reconstruction Methods: State of the Art

The FST and FDT theorems provide equivalence between the spatial frequencies of respectively the measured projection or field outside the object and spatial frequencies of the object itself, thus enabling to fill the Fourier space with multiple angular views, before recovering the spatial information of the object through inverse Fourier transform. One can intuitively understand that the resolution and accuracy of the reconstruction thus depends essentially of the sampling capabilities of the measurement system, and on the amount of angular views. In particular, the data set becomes sparser for higher spatial frequencies, so that the angular sampling capability becomes a key factor in order to retrieve sufficient information to correctly recover fine details of the object so that the problem of tomographic inversion mainly lies in a mapping of spatial frequencies equally distributed in a cylindrical space to a Cartesian reciprocal space. This implies that the sampling of discrete measurements is highly non-evenly distributed, with an overrepresentation of low frequencies, and potentially sparse information at high frequencies, as shown schematically in FIG. 2(d), where numerous lines are represented.

The fundamental equation describing the FST in 2D as represented in FIG. 2(c) is $$F\{U_\alpha(t)\}(\omega_t) = F\{O(x,y)\}(\omega_x \cos\alpha, \omega_y \sin\alpha),$$

where F represents the Fourier transform, $U_\alpha(t)$ corresponds to the measurement for an angle $\alpha$ on the line t which rotates along with $\alpha$, and O(x, y) is the specimen represented in 2D, with $\omega_x$, $\omega_y$ being the spatial frequencies in the Cartesian space.

On the other hand, the fundamental equation describing the FDT as represented in FIG. 2(a) is $$F\{u\}(k_x, k_y, l_0) = \frac{i}{2k_z} e^{ik_z l_0} F\{o(x, y, z)\}(k_x, k_y, k_z - k_0),$$

where $u(x,y,l_0)$ is the scattered field measured at a distance $l_0$. k is the wave vector, with its projection ($k_x$, $k_y$, $k_z$), and its norm $k_0 = 2\pi/\lambda$, and o(x, y, z) is the scattering potential of the object, defined by $$o(x,y,z) = k_0^2[n^2(x,y,z) - 1],$$

where n(x,y,z) is the distribution of refractive index within the specimen.

As it can be seen in the equations above, the FST and the FDT both describe a correspondence between the spatial distribution within the object and measurements outside of the object in the spectral domain. However, spatial implementations of the reconstruction have usually been preferred, especially in cases where diffraction is not taken into account. This is due to the easy discretisation and implementation of the back-projection equations, which provide a direct inversion of the data set. On the other hand, Fourier methods require specific care in their implementation, in order to avoid numerical artefacts which can occur due to discretisation errors during mapping of frequencies measured in a cylindrical basis to the Cartesian basis used for inversion. However, they also enable a more straightforward and faster implementation in the case where diffraction is taken into account (FDT)

More recently, Fourier methods have indeed been essentially employed for resuits recovered in the context of microscopy. This is due essentially to the long computation time of spatial implementations including diffraction, and to their lack of flexibility. Spatial derivations require indeed the incorporation of the acquisition model within the derivation of analytical formulas, which typically do not cover the case of beam scanning, where a frequency shift of the measured scattered fields is induced. Furthermore, spatial inversions such as the inverse Radon transform require constant angular sampling in the data set, which is not always the case with acquisitions performed in microscopy applications. The Fourier methods enable in this context the possibility of incorporating directly the specific imaging conditions during mapping, and make possible to employ straightforwardly data sets with non-equally sampled measurements.

Linear Scanning Tomography

We present here a detailed description of an example of Implementation of the acquisition principle based on linear scanning, which aims at avoiding any movement of the illuminating beam and any rotation of the object, in order to improve mechanical stability during scanning. The data acquisition approach is thus based on a beam containing an angular distribution in the field of view obtained through a structured illumination, thus providing the propagating vectors at different angles, while scanning is performed by moving the object in the x-y plane.

In this proof of principle, we present the case of a spherical wave as illumination it contains a large and continuous distribution of angles and can be simply generated with a high aperture lens, for example. The detection is performed with digital holography, which enables the detection of the complex wave front at a given distance, as required by the FDT. In this example, only the phase information is employed, in a similar way as for the FST.

Linear Data Acquisition Approach

The data acquisition is based on a convergent wave in the field of view, in which the specimen is scanned in order to retrieve the angular information as shown schematically in FIG. 4(a), typically generated by employing a high NA condenser lens. The object is then scanned in the field of view through a translation in the x-y plane, enabling measurement with the object in various positions, corresponding to different propagation directions of the illuminating beam, as shown in FIG. 4(b). As this approach is based on generating an angular distribution through the use of a condenser lens, one can readily see that the 3D CTF is similar to the beam scanning case (cf. FIG. 3(e)), as the resolution along the optical axis is essentially limited by the NA of the illumination. The approach taken in this proof of principle typically leads to an implementation of illumination incorporated with linear scanning as depicted in FIG. 5(a).

Linear Tomography Inversion Method for Convergent Beams

In order to invert the data measured in this example of liner tomography inversion, we employ an approach where we first arrange the data to enable the use of reconstruction algorithms based on the FST through Fourier mapping methods, but without requiring a full angular coverage. In the proof of principle presented here, the reconstruction does thus not take into account diffraction, as arrangement methods require independent value on pixels. We present below the various steps employed for reconstructing the tomogram.

The fact of employing Digital holographic Microscopy (DHM) for acquisition in this example implies that the complex wavefront must first be reconstructed from the hologram to retrieve the quantitative phase image transmitted through the specimen. An example of measured hologram is given in FIG. 5(b) for an empty field of view, which can then be reconstructed in phase through standard algorithms for off-axis hologram reconstruction, giving a phase map as shown in FIG. 5(c), where the curvature of the wave front can be readily identified. This type of uniform phase map corresponding to an empty field of view can be employed for calibrating the angular distribution within the field of view. Furthermore, it can be employed to then compensate for the wave front curvature, in order to retrieve measurements with acceptable phase flatness for further processing.

This acquisition scheme is then employed to acquire frames for different object positions to retrieve the angular information. We consider here for the sake of simplicity an object smaller than the field of view. Furthermore, we limit our discussion to a linear scan in the x direction. In this fashion, the raw 3D stack of data is measured in a space as represented in FIG. 5(a), where (x, y) corresponds to the fixed referential of the detector, and $(x_p, y_p)$ is the referential of the moving stage (cf. FIG. 6(a)). The two referentials are assumed to be collinear, and related only by a translation. The frames are linked to a fixed angular distribution, corresponding to the spherical wave employed for excitation.

In the case of an object of interest smaller than the field of view, each frame can be cropped to a region of Interest (ROI). The principle of linear scanning provide a deterministic relationship between the position (x,y) and the illumination angles, which can be used to recover the use of standard reconstruction algorithms based on angular views with their rotation axis centred in the field of view. Each ROI can thus be translated in the scanning referential, in which the object is static, as shown in FIG. 6(b), thus providing a specific angular distribution for each frame, depending on the position. Thanks to the bijective relation between the position and the angle, this data set can be represented in a space $(x_p, y_p, \alpha)$, as shown in FIG. 6(c). The fact that frames are shown on diagonal lines here results from the assumption of an equi-angular sampling which corresponds to a parabolic profile of the illumination wave.

One can observe in the representation of FIG. 6(c) that triangular regions of unmeasured data are present. They correspond to the extremities of the measurement stack, where the object is only partly present in the field of view. It is indeed necessary to ensure that the specimen is illuminated by all the rays with angles available in the illumination pattern, so that the scanning range must be larger than the field of view. The data set can thus be arranged to suppress these unmeasured portions by translating each frame to the same origin for each value, finally providing a data stack which corresponds to a sinogram by suppressing the triangular unwanted portions.

Other Reconstruction Methods

The method described above where data is rearranged in accordance with the known spherical wave front can be easily applied in the case of the preferred embodiment, but may not be appropriate or suitable for more general structured illumination, where the exact angular distribution is more difficult to know with precision. More adaptive methods, such as iterative approaches for example, may be used to fit the reconstruction process. First, these adaptive methods can be used to improve the knowledge about the precise angular distribution in order to improve the reconstruction. Secondly, these approaches can also be employed to improve the result of the three-dimensional reconstruction by employing prior knowledge about the mathematical and physical properties of the reconstructed data. For example, iterative approaches coupled with non-negativity constrains can ensure a better spatial resolution, where the constraints can for instance be applied to the Fourier intensity which has to be positive, or on the object absorption, which also has to be positive.

Experimental Demonstration

We present in this section the results obtained according to the method presented above and which proves the feasibility of the method. The specimen is moved with a standard x-y moving stage in a microscope setup, with a convergent wave as an illumination pattern.

The illumination pattern is generated by employing a 20×MO (NA=0.4) as a condenser, which provides a high quality convergent beam with minimal aberrations. As depicted in FIG. 5(a), the beam size is adapted by a couple of lenses mounted in a 2f configuration to fill the exit pupil of the excitation optics with a collimated beam, in order to use the infinity-corrected MO in its design conditions. A diaphragm is placed at the conjugated plane of the object position, enabling fine adjustment of the beam diameter to the size of the exit pupil, while avoiding rings artefacts generated by the spatial coherence of the source.

The converging beam then illuminates the specimen, where it fills the field of view in the object space. For this purpose, the excitation MO is placed on a moving stage, enabling also fine adjustments on the z axis in order to ensure full illumination of the measured region. The MO was chosen as a 20× for these preliminary measurements, since the typical working distances of this type of objectives in the millimeter range makes it possible to use standard microscopic preparation on glass slides, which thickness is generally in this range. On the detection side, a cover slip (0.17 mm) is used for standard imaging conditions.

To enable linear scanning with high precision, the specimen is mounted on a closed-loop 3D piezo-electric stage having a positioning precision in the nanometer range, and a moving range of 100×100×10 μm. As the sample must be moved along the whole field of view, the relay optics has been adapted to adjust the magnification to ensure that measurement zone is smaller than the moving range of the piezo-electric stage.

The measurements are performed on paper mulberry pollen grains having a typical size of 10-15 μm, immersed in glycerol. These pollens were chosen for their ease of manipulation, while having sizes comparable to most animal cells which can be observed in vitro.

In a first stage, the setup is calibrated with a flat illumination with a low NA condenser lens (NA≈0.033), and the reference wave is chosen to be collimated, so that the beams at camera level also mimic plane waves. This configuration makes it possible to minimise curvature, to then rely on the phase profile acquired on the camera for estimation of the illumination pattern, and thus for determination of the angles of excitation on different parts of the field of view.

After this calibration, the setup is changed to the configuration presented in FIG. 5(a) in order to enable measurement with converging waves. The excitation profile is then adjusted by changing the height of the excitation MO. It is thus possible to adjust the excitation beam to the size of the field of view and measure a hologram with an empty field of view for angular pattern determination.

We then perform the scan in a one-dimensional way, as discussed previously, where we ensure that the camera orientation is aligned with the one of the moving stage, so that the scanning direction is perpendicular to one of the axis of measurement. The fact of performing a one-dimensional scan parallel to an axis of the detector makes it possible to easily use separability in the FST formalism, in order to reconstruct the object slice by slice to recover the 3D volume. We chose for these preliminary measurements to match the scanning step and the object pixel size, so that an image is taken for each pixel pitch of the detector.

We then arrange the data set according to the procedure described above, in order to retrieve the data set in a structure similar to a sinogram, as shown in FIG. 6(c). We present as an illustration the angular views of the measured pollen grain in FIG. 7 for different scanning positions. One should note that due to the data arrangement, the Images presented here are different from the raw measurements, as each image corresponds at this point to an angular view for a constant angle on the whole image.

Finally, the recovered data set can be inverted through a Fourier implementation of the FST, as described before. We thus fill the 2D Cartesian Fourier space, where the mapping is based on the angles retrieved from the reference hologram characterising the excitation pattern. The inversion leads to the results shown in FIG. 8, for typically a x-z section situated at the centre of the pollen grain (cf. FIG. 8(a-b)), shown here with isotropic sampling of the matrix, and for units in radians per voxel. One can recognise in the real part of the inversion the structure of the pollen, with sectioning in the z direction (cf. FIG. 8(a)). As we employ here an inversion based on the FST, the reconstruction is performed by considering only the phase part of the measurement, so that the retrieved signal should be in principle real-defined. However, due to reconstruction artefacts and numerical errors, the reconstructed signal is commonly complex when employing Fourier mapping methods. We show in FIG. 8(b) the imaginary part of the reconstruction, being typically three orders of magnitude lower than the real part, which is an indication of a relevant reconstruction.

One can identify in FIG. 8(a) the main shape of the specimen, and in particular the nucleus, slightly shifted from the centre of the pollen grain. The resolution is however degraded because of the limited NA of the illuminating MO used in this proof of principle. This can also be identified inside the pollen, where various patterns have an elliptical shape, due to the anisotropic resolution of the reconstruction. One can assume that these patterns are generated by the granular internal structure of this pollen type. One can also see the effect of the cell wall at each border of the section, where it induces a large signal variation. This is due to the strong diffraction at the cell wall interface, which is not taken into account in our reconstruction, and the high refractive index gradient at this region, which cannot be resolved at our current resolution.

As each voxel in the tomogram corresponds to a local phase shift induced in the z direction, it is possible to then reconstruct the 3D refractive distribution through the simple formula $$\Delta n = \frac{\lambda_0}{2\pi\Delta z}\Delta\varphi,$$

where $\Delta z$ is the size of a voxel in the direction of the optical axis, and where the refractive index $\Delta n$ is expressed relatively to the immersion medium. The sampling on the z axis in the reconstruction is identical to the one in the x direction, as it is performed on cubic matrices, so that $\Delta z = \Delta x$. The resulting refractive index (RI) distribution is shown in FIG. 8(c-f) through x-y sections, where $\Delta n$ is relative to glycerol (n=1.473). The sections are presented at respectively z=[−3, 0, 4, 8]μm in regards to the centre of the pollen grain. These sections are typically chosen to be sufficiently apart compared to the z resolution being typically slightly below 1 μm.

The pollen mainly induces refractive index changes in the [1.45, 1.49] range, which is within reasonable values for vegetable cells, and consistent with the observation of similar specimens. The RI values are however very probably lower than the exact ones, as the reconstruction is smoothed because of the limited resolution.

Sections in the x-y plane are visually far better than the x-z ones, thanks to their isotropic resolution. This visualisation also shows some artefacts of reconstruction which were not visible in FIG. 8(a-b), resulting from the reconstruction from a one-dimensional scan. Ripples can indeed be identified horizontally, which corresponds to the dimension of the linear scan, while these ones are not present in the vertical direction, as the reconstruction is performed by employing separability. In the different sections of FIG. 8(c-f), one can identify various features of the pollens, which are consistent with the transmission images of FIG. 7. The nucleus can be observed as shifted on the right and on the top of the pollen, as it is still present at z=4 μm but vanishes already at z=−3 μm. On the left of the pollen, small features with low RI values can also be observed, which may correspond to the smaller structures observed for example in the images of FIG. 7.

In our present experimental protocol, we limited our scanning geometry to a line, in order to enable reconstruction through separability and thus retrieve the 3D volume from the 2D reconstruction of sections, implying that we neglected the angular distribution in one direction of the spherical wave of excitation. More refined scanning trajectories, based in this case on fully three-dimensional inversion methods, may increase the reconstruction quality, by typically suppressing the directional artefacts which were identified in FIG. 8(c-f) (for example spiral scanning).

The proposed method presents mainly the advantage of employing a scanning which is in a geometry identical to standard planar biological preparations, classically mounted on slides. Consequently, as the acquisition of the angular information is already based on a scanning in the x-y plane, it could lead to an easy approach for the tomography of large specimens, such as wide fields of view of cell culture preparations, or microscopic living organisms like multicellular organisms: embryo, animals or plants. On the other hand, as it relies on a fixed illumination pattern during scanning, the calibration procedures are made simpler compared to other approaches, thus potentially easing the way to routine measurements. Furthermore, it could enable an easier combination of deconvolution techniques with tomographic acquisition, as the PSF stays in principle constant during the whole scanning, in order to further improve the reconstruction resolution.

Importance of the Polarisation of the Structured Wave Front of the Illumination Beam:

In a preferred embodiment of the invention, simply linear polarised light is used to engineer the Illuminating wave front. It must however be pointed out that partial depolarisation and apparition of elliptic polarisation cannot be avoided for strongly convergent illuminations. Such inconvenience can be avoided by the recourse to radially polarised light. Radially or azimuthally polarised light can be obtained by using a radial polarisation converter. The distribution of the wave vector (light grey arrow), and associated electric field (radially oriented) and magnetic fields (azimuthally oriented) is shown on FIG. 9. Another advantage of radially polarised light is the strong confinement of the electric field in the focal region.

Analysis of the Scattered Beam Polarisation

The state of polarisation of the beam scattered by the specimen can be determined by using coherent detection scheme.

FIG. 10 presents how to measure the spatial distribution of the polarisation state of the measured scattered field. The figure shows how to form and capture a hologram with the beam issued from one scattering point of the illuminated specimen and captured by the infinity corrected microscope objective (MO). An image of the scattering point is formed by the tube lens (optional) at some distance behind, in front of, or just in the plane of the detector array. The detector array effectively captures the hologram formed by the interference of the object beam provided by the MO associated with a tube lens and a linearly polarised reference beam delivered for instance by a beam splitter, or any polarising optical element. A slightly off-axis propagation of the reference beam permits the formation of an hologram with a spatially modulated carrier frequency which can be easily analysed in the Fourier domain. In a preferred embodiment, such analysis allows for a wavefront reconstruction of the polarised scattered wavefront from a single hologram. An alternate method is the well known in-line holography, but several (three to four) holograms must be taken to fully reconstruct the wave front (phase shifting technique).

FIG. 11 a) and b) presents the possibility of simultaneously resolving the two orthogonal components of the polarisation. By combining two orthogonally polarised reference beams to form a single hologram containing all the information to reconstruct from a single hologram the exact polarisation state of the beam scattered by the specimen. FIG. 11 a) and b) show the projections of the optical setup on two orthogonal planes parallel to the optical axis of the setup. In order to separate the carriers in the 2D Fourier transforms of the hologram, slightly off-axis reference beams are generated for each polarisation state.

Combining radially polarised convergent illumination beam and the detailed analysis of the polarisation state of the light scattered by the specimen allows in particular to establish the birefringence characteristics of the specimen. In the context of the proposed invention, the use of radially polarised light enables polarisation-resolved measurements while avoiding the mixing of the two states at the excitation level due to strongly focused light.

Coherent or Incoherent Detection of the Scattered Beam can be Used in the Present Invention:

Coherent Detection: State of the Art

Coherence can be exploited in various manners to reconstruct the complex wavefront emanating from the specimen. The requirements are indeed only slightly restrictive in microscopy. Only some degree of mutual coherence is needed to permit the evaluation of the coherence between the wavefront denoted O, scattered by the specimen, and a reference wave (denoted R). The phase data can be derived from the autocorrelation of the wavefeld O, or from the cross-correlation between O and R. In holographic microscopy, the coherence length either in the spatial or in the time domain has only to be comparable to the size of the specimen.

In a the example of implementation presented above, the reference beam R is generated by deriving part of the illumination beam with a beam splitter and recombining it to form an hologram $I_H$ (x,y,t).

However other implementations can be considered, such as in the case where the reference beam R is generated by processing optically the object beam: for example spatial low pass filtering (Indebetouw, 1980) or diffraction microscopy (Popsecu).

In all cases of implementations discussed, the main ambition is to restore exactly the wavefield from one or several holograms taken at different time or at different locations. In many cases however a single hologram is sufficient to reconstruct fully the complex wavefield (Cuche, O L, 1999) Traditionally, the hologram or intensity distribution $I_H$ (x,y,t) on a 2D plane or surface resulting from the interference of the object beam: O with a reference wave R can be developed as:

$$I_H(x,y,t) = (R+O)^* \times (R+O) = |R|^2 + |O|^2 + R^*O + RO^*$$

The last two terms: $R^*O(x,y)$ and $RO^*(x,y)$ are the "cross terms", which express the mutual coherence of the object wave and the reference wave which does not vanish provided that some degree of coherence exists between both waves. The wavefield restoration is based on the digital evaluation of these cross terms, which provide a simple access to the true complex value of the wavefront O, respectively O*, just by multiplication of R, respectively R*. At the end, coherent detection methods aim at retrieving these cross terms for evaluation of the complex field.

The equation given above also contains the two first terms $|R|^2$ and $|O|^2$ which are the intensity distribution of the object and reference waves over the hologram plan and are commonly designated as the "zero order terms". Methods here called "incoherent detection methods" are based on the use of these terms for evaluation of the phase of complex field of the object wave. Their expression in the temporal Fourier domain is the spectrum of the autocorrelation of the wavefield in the time domain which is generally a Dirac for monochromatic sources and an approximately a Gaussian shaped sinusoidal signal for broadband sources. These are permanent terms, present even if O and R waves are completely incoherent $|R|^2$ is slowly varying over space for most of usual reference wave: such as plane or spherical waves. $|O|^2$ is the spectrum of the autocorrelation of the object wave in the time domain and may be a complex signal that acts often as a perturbing term in the evaluation of $I_H$. Techniques have been developed to restore O(x,y) from $|O|^2(x,y)$: (Fienup, A O, 1982). In particular, the so-called Gerchberg-Saxton and Yang-Gu (Yang Gu, Act. Phys. S., 1981) algorithms have been developed in this purpose. They are however computer intensive and require particular consideration of the imaging context: in many situations, the problem may appear as ill-posed. Their applications in optical microscopy appear still limited. Another approach is based on the measurement of $|O|^2(x,y)$ on planes situated at various distances z: (Teague, JOSA 1983, Nugent JOSA, 1996). Quantitative phase imaging can be derived from the so-called "transport of intensity equation" (TIE). The method has been applied successfully to various domains in microscopy.

Finally the wave front can also be reconstructed with a non coherent, non interferometric method, by determining both the intensity and direction of the propagation (direction of the wavevector) on a surface intercepting the beam: Hartmann-Shack sensors can be used for that purpose. Similarly the formation of Talbot self-image generated by a grating is also a mean to measure the propagation direction (k-vector). The approach is similar with the so-called quadriwave lateral shearing interferometry (P. Bon, O X, 2009)

The proposed invention for tomography based on linear scanning with detection of the complex field is indeed not limited to a particular method for detecting the phase of complex field and can therefore be employed in all situations and examples mentioned above. All these approaches based on coherent and incoherent detection in phase and intensity (complex wave front) of beams scattered by the specimen are possible methods covered by the scope of the invention.

REFERENCES

1. M. Born and E. Wolf, Principles of Optics (Cambridge University Press, 1999), chap. Scattering from inhomogeneous media, pp. 695-734, 7th ed.
2. F. Charrière, F. Monfort, A. M. J. Kuhn, T. Colomb, E. Cuche, P. Marquet, and C. Depeursinge, "Cell refractive index tomography by digital holographic microscopy," Opt Lett. 31, 178-180 (2006).
3. F. Charrière, N. Pavilion, T. Colomb, C. Depeursinge, T. Heger, E. Mitchell, P. Marquet, and B. Rappaz, "Living specimen tomography by digital holographic microscopy: Morphometry of testate amoeba," Opt. Express 14, 7005-7013 (2006).
4. W. Choi, C. Fang-Yen, K. Badizadegan, S. Oh, N. Lue, R. Dasari, and M. Feld, "Tomographic phase microscopy," Nat. Methods 4, 717-719 (2007).
5. R. Dändliker and K. Weiss, "Reconstruction of the three-dimensional refractive index from scattered waves," Opt. Commun. 1, 323-328 (1970).
6. Devaney, "A filtered backpropagation algorithm for diffraction tomography," Ultrason. Imaging 4, 336-350 (1982).
7. M. Debailleul, B. Simon, V. Georges, O. Haeberlé, and V. Lauer, "Holographic microscopy and diffractive microtomography of transparent samples," Meas. Sci. Tech. 19, 074009 (8 pages) (2008).
A. C. Kak and M. Slaney, *Principles of computerized tomographic imaging* (IEEE Press, New York, 1987).
8. S. S. Kou and C. J. R. Sheppard, "Image formation in holographic tomography," Opt. Lett. 33, 2362-2364 (2008).
9. V. Lauer, "Microscope generating a three-dimensional representation of an object", WO/1998/013715, (1998).
10. V. Lauer, "Microscopie generating a three-dimensional representation of an object and images generated by such a microscope", WO/1999/053355, (1999).
11. Y. Sung, W. Choi, C. Fang-Yen, K. Badizadegan, R. Dasari, and M. Feld, "Optical diffraction tomography for high resolution live cell imaging," Opt. Express 17, 266-277 (2009).
12. S. Vertu, J.-J. Delaunay, I. Yamada, and O. Haeberlé, "Diffraction microtomography with sample rotation: influence of a missing apple core in the recorded frequency space," Cent Eur. J. Phys. 7, 22-31 (2009).
13. E. Wolf, "Three-dimensional structure determination of semi-transparent objects from holographic data," Opt. Commun. 1, 153-156 (1969).
14. Cuche, E., Bevilacqua, F., and Depeursinge, C. Digital holography for quantitative phase-contrast imaging. *Opt Lett.* 24: 291-293. (1999)
15. Indebetouw, G. and Klysubun, P. Space-time digital holography: A three-dimensional microscopic imaging schewith an arbitrary degree of spatial coherence. *Appl. Phys Lett.* 75: 2017-2019. (1999)
16. Popescu, G., T. Ikeda, R. R. Dasari, and M. S. Feld, *Diffraction phase microscopy for quantifying cell structure and dynamics.* Optics Letters. 31(6): p. 775-777. (2006) Wang, Z., L. Millet, M. Mir, H. F. Ding, S. Unarunotai, J. Rogers, M. U. Gillette, and G. Popescu, *Spatial light interference microscopy (SLIM).* Optics Express. 19(2): p. 1016-1026. (2011)
18. Fienup, J. R. Phase retrieval algorithms—a comparison. *Appl. Opt* 21: 2758-2769. (1982)
19. Yang, G. and Gu, B. On the amplitude-phase retrieval problem in the optical system. *Acta Phys. Sinica* 30:410-413 (1981)
20. Teague, M. R. Image-Formation in Terms of the Transport-Equation. *J. Opt. Soc. Am. a-Opt. Image Sci. Vis.* 2: 2019-2026. (1985).
21. P. Bon, G. Maucort, B. Wattellier and S. Monneret. Quadriwave lateral hearing interferometry for quantitative phase microscopy of living cells. Opt Express, 17 No. 15, 13080-13093 (2009)

The invention claimed is:
1. An apparatus for performing quantitative phase tomography on a specimen, comprising:
an illumination source for providing an illuminating beam;
a condenser lens having an optical axis direction arranged to transform the illuminating beam into a convergent illuminating beam;
a microscope objective arranged to collect a beam that is back-scattered by the specimen, the illumination source arranged to illuminate the specimen from a same side as the beam collected by the microscope objective; and
a wave front analyzer for analyzing a wave field amplitude and phase of the beam back-scattered by the specimen, the wave front analyzer including,
an array sensor for measuring an intensity of the beam back-scattered by the specimen and collected by the microscope objective, and outputting a measurement signal,
a displacement device to move the specimen in a plane normal to the optical axis direction, and
a processing device configured to process the measurement signal output by the array sensor to deliver quantitative phase tomography images representing the specimen in three dimensions based on the beam back-scattered by the specimen, and to provide quantitative values of a refractive index distribution.
2. The apparatus of claim 1, where the wave front analyzer is configured to analyze the beam back-scattered by the specimen
a) by analyzing the beam back-scattered by the specimen based on amplitude and phase for a given wavelength,
b) by at least one of transport of intensity equations (TIE), spiral phase filtering, and common path interferometry, with a reference beam source having a plurality of optical parts that are arranged to derive the reference beam from the beam back-scattered by the specimen, or
c) by deriving the illumination beam before crossing the specimen with digital holography or shearing interferometry.
3. The apparatus of claim 1, further comprising:
a reference beam generator that generates a reference beam coherent relative to the illuminating beam, the reference beam generator deriving the reference beam either from the beam back-scattered by at least one of the specimen and from the illumination beam; and
a device for directing the reference beam and combining the reference beam with the beam back-scattered by the specimen such that measurement signal of the array sensor yields, after data processing, a coherent detection of the beam back-scattered by the specimen.

4. The apparatus of claim 3, wherein the reference beam generator includes a beam splitter arranged to derive the reference beam from the illuminating beam.

5. The apparatus of claim 1, wherein the illumination source provides the illuminating beam with a linear polarization or an elliptic polarization.

6. The apparatus of claim 1, wherein the illumination source provides the illuminating beam with a radial polarization,
wherein the microscope objective includes a tube lens,
wherein the wave front analyzer further includes a beam splitter to superimpose, onto the beam back-scattered by the specimen, a linearly polarized reference beam for irradiating the array sensor with alternate or simultaneous orthogonally linearly polarized beams derived from the illumination beam, by at least one of linear polarizers, beam splitters, mirrors, and polarization maintaining fibers.

7. The apparatus of claim 1, wherein a complex wave front is reconstructed from intensity measurements only of the beam back-scattered by the specimen,
wherein the wave front analyzer includes a camera that is arranged at a distance from a focal plane to provide the intensity measurements of the beam back-scattered by the specimen to reconstruct the complex wave front.

8. The apparatus of claim 1, wherein
the wave front analyzer includes optical elements arranged to reconstruct a complex wave front, including at least one of an array of microlenses, gratings, composing Hartmann-Shack wave front sensor, quadriwave sensor, and shearing interferometry device, and
the processing device is further configured to compute a scattered field complex wave front.

9. The apparatus of claim 1, further comprising:
an optical device to derive a reference beam from the illumination source before illumination of the specimen, and to superimpose the reference beam to the beam back-scattered by the specimen that is impinging on the array sensor, and
wherein the processing device is further configured to compute a complex wave front from the reference beam and the beam back-scattered by the specimen from a hologram obtained by Digital Holographic Microscopy (DHM).

10. The apparatus of claim 1, wherein the processing device is configured to
a) generate a stack of phase data in a projection plane positioned in front of the microscope objective, the generation being repeated after each displacement of the specimen,
b) reconstruct a complex wave front from the stack of the phase data,
c) move the specimen delimitated in a region of interest to a fixed central position,
d) re-arrange data in the stack of phase data to regroup, in each plane, data corresponding to a new plane normal to an illumination direction at an initial position of the specimen in a fan beam,
e) apply a Fourier Slice Theorem (FST) to the data from d) to compute a Fourier transform of a phase distribution in each plane perpendicular to the illumination direction,
f) group data from e) in a wave vector space, and
g) compute an inverse Fourier transform of the wave vector space to obtain a refractive index minus the refractive index of background medium.

11. The apparatus of claim 1, wherein the processing device is configured to
a) generate a stack of amplitude and phase data in a projection plane positioned in front of the microscope objective, the generation being repeated after each displacement of the specimen,
b) reconstruct a complex wave front from the amplitude and phase data,
c) move the specimen delimitated in a region of interest to a fixed central position,
d) re-arrange data in the stack of amplitude and phase data to regroup, in each 2D array of the stack, the complex wave front corresponding to a new section plane normal to an illumination direction at an initial position of the specimen in a fan beam,
e) apply a Fourier Diffraction Theorem (FDT) to compute a Fourier transform of a data distribution of the complex wave front in each plane normal to the illumination direction,
f) map results of step e) on an Ewald sphere corresponding to each illumination direction;
g) group results of f) in three dimensions in a wave vector space, encompassing the results of the mapped Ewald sphere of f) and a radius of which is a diameter of corresponding Ewald spheres, and
h) compute an inverse Fourier transform of the wave vector space to obtain a scattering potential, including a refractive index minus a square of the refractive index of a background medium.

12. A method for performing quantitative phase tomography on a specimen, comprising steps of:
providing an illuminating beam by an illumination device;
transforming the illuminating beam into a convergent illuminating beam;
directing the convergent illuminating beam along an optical axis direction to irradiate the specimen;
collecting a beam back-scattered by the specimen by a microscope objective that is arranged at a same side as the illumination source;
measuring an intensity of the beam back-scattered by the specimen and collected in the step of collecting;
displacing the specimen in a plane normal to the optical axis direction;
processing measurement data collected at the step of measuring the intensity of the beam back-scattered by the specimen to reconstruct a complex wave front of the light scattered by the specimen;
building-up a stack of complex wave front data obtained by repeating the step of displacing the specimen in the shaped illuminating beam, the step of measuring the intensity of the beam, and the step of processing the measurement data;
computing dielectric properties of the specimen in a form of the Refractive Index (RI) distribution in three dimensions; and
representing the specimen in a three dimensional graphical representation.

13. The apparatus of claim 1, wherein the wave front analyzer is a Hartmann-Shack analyzer.

14. The apparatus of claim 6, wherein the reconstruction of the complex wave front is calculated according to a Gerchberg-Saxton iterative method.

15. The apparatus of claim 6, wherein the wave front analyzer includes a mechanical displacement device to move the camera along the optical axis direction, and wherein the reconstruction of the complex wave front is calculated based on multiple distance intensity measurements according to Transport of Intensity Equations (TIE).

16. An apparatus for performing quantitative phase tomography on a specimen, comprising:
an illumination source for providing an illuminating beam to illuminate the specimen;
a microscope objective including two microscope lenses that are symmetrically positioned on each side of the specimen, arranged to transform the illumination beam into a convergent beam and to collect a beam scattered by the specimen; and
a wave front analyzer for analyzing a wave field amplitude and phase of the beam scattered by the specimen, the wave front analyzer including,
an array sensor configured to measure an intensity of the beam scattered by the specimen and collected by the microscope objective, and outputting a measurement signal,
a displacement device configured to move the specimen in a plane normal to the optical axis direction, and
a processing device configured to process the measurement signal output by the array sensor to deliver quantitative phase tomography images representing the specimen in three dimensions, and to provide quantitative values of a refractive index distribution,
wherein the beam scattered by the specimen is collected by the two microscope lenses to collect simultaneously forward-scattered light and back-scattered light with a convergent illuminating beam provided by at least one of the two microscope lenses.

17. The apparatus of claim 16, further comprising:
a beam shaper having an optical axis direction, the beam shaper transforming the illuminating beam into a shaped illuminating beam directed along the optical axis direction to irradiate the specimen.

18. The apparatus of claim 16, where the wave front analyzer is configured to analyze the beam scattered by the specimen
a) by analyzing the beam scattered by the specimen based on amplitude and phase for a given wavelength,
b) by at least one of transport of intensity equations (TIE), spiral phase filtering, and common path interferometry, with a reference beam source having a plurality of optical parts that are arranged to derive the reference beam from the beam scattered by the specimen, or
c) by deriving the illumination beam before crossing the specimen with digital holography or shearing interferometry.

19. The apparatus of claim 16, further comprising:
a reference beam generator that generates a reference beam coherent relative to the illuminating beam, the reference beam generator deriving the reference beam either from the beam scattered by the specimen or the illumination beam; and
a device for directing the reference beam and combining the reference beam with the beam scattered by the specimen such that measurement signal of the array sensor yields, after data processing, a coherent detection of the beam scattered by the specimen.

20. The apparatus of claim 19, wherein the reference beam generator includes a beam splitter arranged to derive the reference beam from the illuminating beam.

21. A method for performing quantitative phase tomography on a specimen, comprising steps of:
providing an illuminating beam by an illumination device;
directing the illuminating beam along an optical axis direction to irradiate the specimen;
collecting a beam scattered by the specimen by a microscope objective including two microscope lenses that are symmetrically positioned on each side of the specimen, to collect simultaneously transmitted light and back-scattered light with a convergent illuminating beam provided by one of the two microscope lenses;
measuring an intensity of the beam scattered by the specimen and collected in the step of collecting;
displacing the specimen in a plane normal to the optical axis direction;
processing measurement data collected at the step of measuring the intensity of the beam scattered by the specimen to reconstruct a complex wave front of the light scattered by the specimen;
building-up a stack of complex wave front data obtained by the step of displacing the specimen in the convergent illuminating beam by linear scanning;
computing dielectric properties of the specimen in a form of the Refractive Index (RI) distribution in three dimensions; and
representing the specimen in a three dimensional graphical representation.

22. An apparatus for performing quantitative phase tomography on a specimen, comprising:
an illumination source for providing an illuminating beam;
a condenser lens having an optical axis direction arranged to transform the illuminating beam into a convergent illuminating beam to illuminate the specimen;
a microscope objective arranged to collect a beam that is scattered by the specimen; and
a wave front analyzer for analyzing a wave field amplitude and phase of the beam scattered by the specimen, the wave front analyzer including,
an array sensor for measuring an intensity of the beam scattered by the specimen and collected by the microscope objective, and outputting a measurement signal,
a displacement device to move the specimen in a plane normal to the optical axis direction, and
a processing device configured to process the measurement signal output by the array sensor to deliver quantitative phase tomography images representing the specimen in three dimensions based on the beam scattered by the specimen, and to provide quantitative values of a refractive index distribution.

23. A method for performing quantitative phase tomography on a specimen, comprising steps of:
providing an illuminating beam by an illumination device;
transforming the illuminating beam into a convergent illuminating beam;
directing the convergent illuminating beam along an optical axis direction to irradiate the specimen;
collecting a beam scattered by the specimen;
measuring an intensity of the beam scattered by the specimen and collected in the step of collecting;
displacing the specimen in a plane normal to the optical axis direction;
processing data collected at the step of measuring the intensity of the beam scattered by the specimen to reconstruct a complex wave front of the light scattered by the specimen;

building-up a stack of complex wave front data obtained by repeating the step of displacing the specimen in the convergent illuminating beam, the step of measuring the intensity of the beam, and the step of processing the measurement data;

computing dielectric properties of the specimen in a form of the Refractive Index (RI) distribution in three dimensions; and representing the specimen in a three dimensional graphical representation.

* * * * *